US007537344B2

United States Patent
Liang

(10) Patent No.: US 7,537,344 B2
(45) Date of Patent: May 26, 2009

(54) METHODS FOR SPECIFYING IMAGE QUALITY OF HUMAN EYES FROM WAVEFRONT MEASUREMENTS

(75) Inventor: Junzhong Liang, Fremont, CA (US)

(73) Assignee: Advanced Vision Engineering, Inc, Fremont, CA (US)

( * ) Notice: Subject to any disclaimer, the term of this patent is extended or adjusted under 35 U.S.C. 154(b) by 0 days.

(21) Appl. No.: 11/370,745

(22) Filed: Mar. 8, 2006

(65) Prior Publication Data

US 2006/0232744 A1    Oct. 19, 2006

Related U.S. Application Data

(60) Provisional application No. 60/660,270, filed on Mar. 9, 2005.

(51) Int. Cl.
*A61B 3/00*    (2006.01)
*A61B 3/10*    (2006.01)

(52) U.S. Cl. ...................................... 351/246; 351/205

(58) Field of Classification Search .......... 351/205–246
See application file for complete search history.

(56) References Cited

U.S. PATENT DOCUMENTS

| | | | | |
|---|---|---|---|---|
| 6,817,714 | B2 * | 11/2004 | Altmann | 351/177 |
| 7,311,400 | B2 * | 12/2007 | Wakil et al. | 351/205 |
| 7,331,674 | B2 * | 2/2008 | Dai | 351/246 |

* cited by examiner

*Primary Examiner*—Mohammed Hasan

(57) ABSTRACT

Relative MTF scores for an eye are determined by obtaining at least one wave aberration of an eye, calculating at least one modulation transfer function from the wave aberration of the tested eye, specifying image quality of the eye using a relative MTF score system derived from the calculated modulation transfer function of the tested eye and a set of modulation transfer functions from a cohort of eyes with normal visual acuity. Methods for comparing image quality of different eyes under equal conditions and at different pupil sizes include comparing MTF of different eyes for best MTF in all pupil sizes and MTF of different eyes for night vision at a large pupil size that is different from eye to eye.

20 Claims, 4 Drawing Sheets

Fig. 3a   Fig. 3b   Fig. 3c
Figure 3
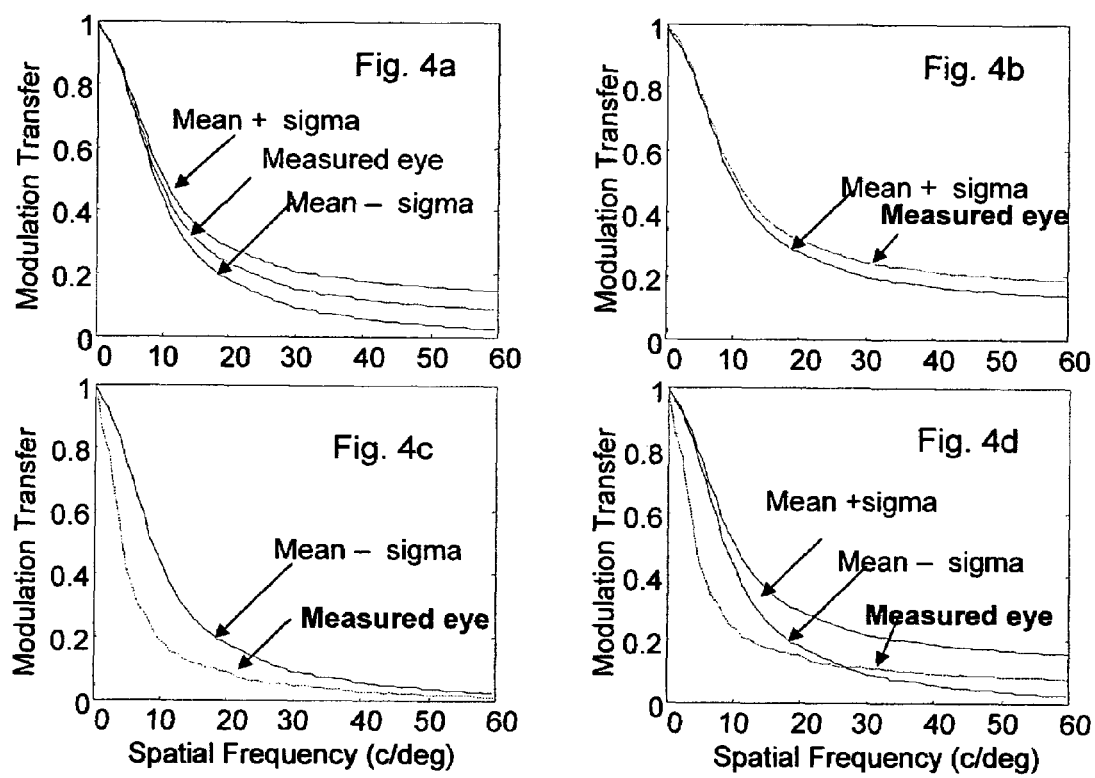
Figure 4

METHODS FOR SPECIFYING IMAGE QUALITY OF HUMAN EYES FROM WAVEFRONT MEASUREMENTS

CROSS-REFERENCES TO RELATED INVENTIONS

The present invention claims priority to the provisional U.S. patent application 60/660,270, titled "ALGORITHMS AND METHODS FOR REFRACTIVE VISION DIAGNOSIS" filed on Mar. 9, 2005 by Liang. The disclosures of these related applications are incorporated herein by reference.

TECHNICAL FIELD

This application relates to systems and methods for measuring human vision, in particular, for specifying vision clarity of the eye from wave aberration of the eye.

BACKGROUND

Visual acuity has been the single most important parameter for measuring performance of human vision for over 150 years because it is a signal number and measures the combined performance of optics, retina, and visual signal processing by the brain.

Visual acuity is however also limited for measuring quality of vision for a number of reasons. First, visual acuity is incomplete because it only measures vision performance for one particular resolution task. Excellent acuity does not guarantee excellent vision. It is possible that someone may have a visual acuity of 20/20 or better but has problems in reading low-contrast texts or has night vision symptoms like glare, halo, and ghost images. Second, visual acuity measures vision performance too coarsely. Among all eyes with the same acuity of 20/20, their true quality of vision can vary significantly from eye to eye. Visual acuity is thus not effective for specifying vision quality in fine details. Third, visual acuity does not measure vision in all lighting conditions. Visual acuity is usually measured in one pupil size clinically. Pupil diameters of eye are known to change significantly depending on the level of surrounding light and quality of vision is important for all pupil sizes.

In light of the limitations of visual acuity, it is readily apparent that a need exists in the art to provide methods for grading quality of vision in finer details than visual acuity, for measuring vision with more general tasks than visual resolution and at multiple pupil sizes.

One known method beyond visual acuity is to specify image quality of eye using Modulation Transfer Functions (MTF). MTF of eye can be obtained in a number of different means. One practical method is to calculate MTF of an eye from wave aberration as disclosed in "Aberrations and retinal image quality of the human eye," J. Opt. Soc. Am. A, vol. 14, no. 11, p. 2873 (November 1997) by J. Liang et al. Wave aberrations are usually obtained from a device called aberrometers including ray tracing aberrometers, Talbot interferometry-based aberrometers, and phase retrieval method-based method, and the Hartmann-Shack sensor based-aberrometer.

FIG. 1 shows a schematic diagram for a typical wavefront system using a Hartmann-Shack sensor as disclosed in "Objective measurement of wave aberrations of the human eye with the use of a Hartmann-Shack wave-front sensor," J. Opt. Soc. Am. A, vol. 11, no. 7, p. 1949 (July 1994) by J. Liang et al. A fixation system (110) assists the tested eye in stabilizing its accommodation and in maintaining the view direction. An illumination light source (120) generates a compact light source to reflect off mirror (BS2) and shine on the eye's retina as the probing light. The probing light is diffusely reflected by the retina, from which a distorted wavefront is formed at the eye's cornea plane. An optical relay system (130), consisting of lenses (L1) and (L2), relays the outgoing wavefront from the eye and reflected off of mirror BS1 to the plane of a lenslet array. A Hartmann-Shack wavefront sensor (140), consisting of a lenslet array and an image sensor, produces a wavefront sensor image as an array of focus spots. An image analysis module (150) detects the focus spots and calculates the wavefront slopes, from which the wavefront is reconstructed by a wavefront estimator (160).

Wavefront system for the eye often measure wave aberration for a large pupil at very low light level. From wave aberration in a large pupil, optical quality of an eye can be calculated for any pupil size that is smaller than the measured pupil size. FIG. 2 shows radially averaged MTF of the eye for 6 different pupil sizes derived from wave aberrations for 14 eyes within a dilated 7.3 mm pupils as disclosed in "Aberrations and retinal image quality of the human eye," J. Opt. Soc. Am. A, vol. 14, no. 11, p. 2873 (November 1997) by J. Liang et al.

Using MTF in its original form is not practical in clinical settings for at least two reasons. First, MTF is a scientific term and it specifies the transfer ratio of image contrast from the object space to the image space. Few clinicians would be able to interpret its clinical meaning in its original form. Second, there is so far neither an effective method nor an acceptable standard for grading eye's MTF clinically. As a common practice, MTF of different eyes are compared at the same pupil size for fairness. Such a fair comparison is however often meaningless because the same pupil size may be used in different vision conditions for different eyes. Vision at a 6 mm pupil size may represent day vision for one person with a large natural pupil and night vision for another. Additionally, comparing night vision for different eyes cannot be performed at the same pupil size because pupil sizes at night can vary significantly from eye to eye as illustrated in FIG. 3, showing images of three eyes at night. The natural pupil sizes of the three eyes are 4.7 mm (FIG. 3a), 6 mm (FIG. 3b), and 8.5 mm (FIG. 3c), respectively. It is not difficult to conclude that comparing MTF at the same pupil is useless for night vision.

In light of the forgoing, it will be readily apparent that a need exists in the art to provide a clinical MTF system that is understandable in clinical settings. More importantly, the clinical MTF system enables to specify quality of vision in a plurality of grades under same visual acuity. It is also apparent that a need exists in the art to provide a more effective method for comparing vision under equal conditions at different pupil sizes.

SUMMARY

The present invention is directed to a method for specifying image quality of an eye using a relative MTF score system, comprising:

obtaining at least one wave aberration of an eye;

calculating at least one modulation transfer function from the wave aberration of the tested eye;

specifying image quality of the eye using a relative MTF score system derived from the calculated modulation transfer function of the tested eye and a set of modulation transfer functions from a cohort of eyes with normal visual acuity.

In an additional aspect, the present invention includes a method for specifying and comparing quality of vision for the best vision quality independent of the pupil size of individual eyes.

In yet another aspect, the present invention comprises specifying and comparing image quality for night vision at a large pupil size that can be different from eye to eye.

The details of one or more embodiments are set forth in the accompanying drawings and in the description below. Other features, objects, and advantages of the invention will become apparent from the description and drawings, and from the claims.

DRAWING DESCRIPTIONS

FIG. 3 shows images of three eyes at night with different nature pupil sizes. Pupil sizes of the three eyes at night are 4.7 mm (FIG. 3a), 6 mm (FIG. 3b), and 8.5 mm (FIG. 3c) respectively.

FIG. 4 shows an example for specifying and displaying eye's MTF in a clinical 3-MTF score system in accordance with the present invention.

DETAILED DESCRIPTION

Clinical MTF Score Systems

Figure 1:
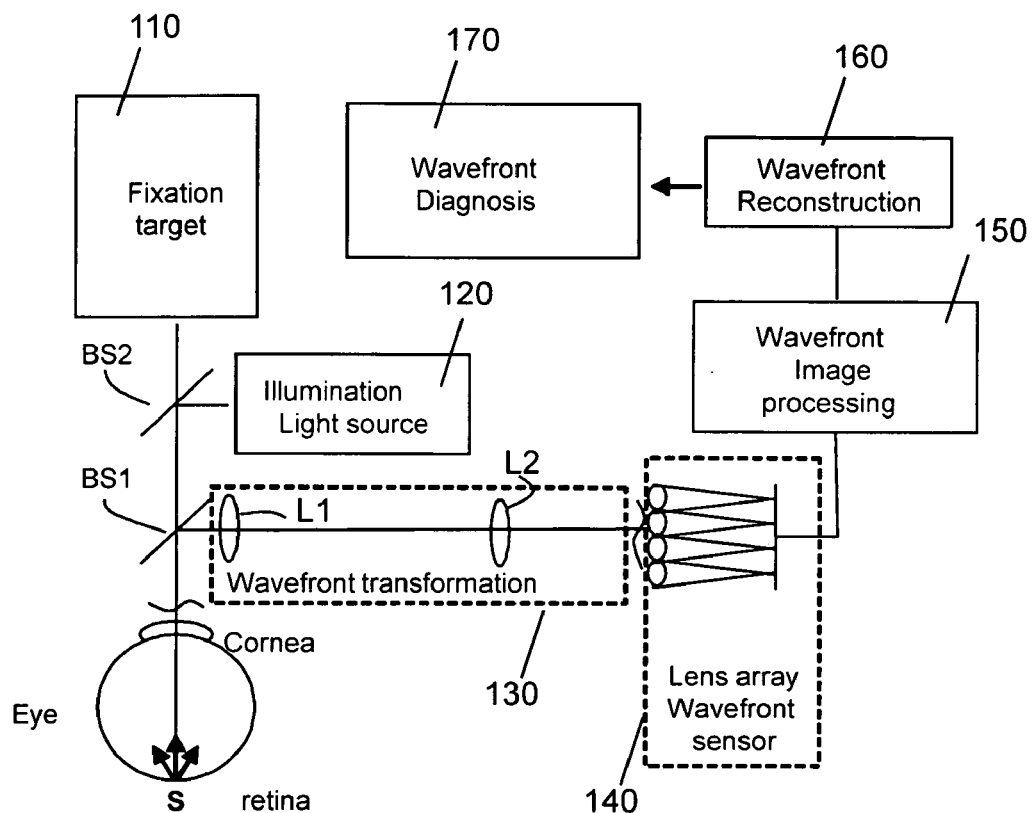
FIG. 1 shows a schematic diagram for a typical wavefront system with a Hartmann-Shack sensor.

MTF of human eyes can be calculated form wavefront measurements, as disclosed in "Aberrations and retinal image quality of the human eye," J. Opt. Soc. Am. A, vol. 14, no. 11, p. 2873 (November 1997) by J. Liang et al, by measuring wave aberration of an human eye with a wavefront device and calculating MTF of the eye from the measured wave aberration using the standard Fourier optics theory.

Conventional MTF of the eye measures the capability of an eye's optics for transferring image contrast from the object space to the image space. It describes the contrast deficit of a real eye in an absolute sense because its reference is an ideal image system.

We propose to specify quality of vision using a clinical MTF score system by changing the reference from an ideal image system to the statistical MTF of a cohort of normal eyes, and determining image quality of an eye using a relative score system derived from the calculated modulation transfer function of the eye and a set of statistical modulation transfer functions from the cohort of normal eyes.

We define a cohort of normal eyes as a large number of young and healthy eyes having a visual acuity of 20/20 or better and without refractive surgery. Statistical representations of the cohort of normal eyes are the mean MTF and the standard deviation (sigma).

In one preferred embodiment, we propose to categorize an eye's optical quality using a clinical 3-MTF-score system. Three clinical MTF scores are defined as "normal," "better than normal" and "worse than normal."

FIG. 4 shows examples of eyes specified under the clinical 3-MTF-score system. FIG. 4a shows an eye with "normal" MTF if its MTF is within one standard deviation of the mean MTF. FIG. 4b shows an eye with "better than normal" MTF if its MTF is above one standard deviation. FIG. 4d shows an eye with "worse than normal" MTF if its MTF is below one standard deviation. FIG. 4d shows an eye is normal for spatial frequencies beyond 30 c./deg and worse than normal for spatial frequencies below 30 C./deg.

In another embodiment, we use a more general mathematic representation of clinical MTF score system as $$\text{Clinical MTF score} = (\text{MTF} - \overline{\text{MTF}})/\text{Sigma}, \quad [1]$$

where MTF is the modulation transfer function of a tested eye, and $\overline{\text{MTF}}$ is the mean MTF for the normal population, and Sigma is the standard deviation of eye's MTF in normal population. The MTF score in equation (1) is continuous. Three digitized versions of MTF score systems are shown in Table 1 through 3.

The clinical MTF systems present an eye's optical quality in relative grades instead of the original absolute contrast transfer coefficients: normal, better than normal, worse than normal, above average, below average and etc. These clinical MTF scores are customized for average clinicians, and can do better in describing the eye's optical quality in clinical settings.

TABLE 1

Clinical 2-MTF-score system

| MTF score | δMTF = MTF − MTF | Categories |
|---|---|---|
| +1 | δMTF > 0 | Better than average |
| −1 | δMTF < 0 | Worse than average |

TABLE 2

Clinical 3-MTF-score system

| MTF score | δMTF = MTF − mean (MTF) | Categories |
|---|---|---|
| +1 | δMTF > 1 sigma | Better than normal |
| 0 | −1 sigma <= δMTF <= 1 sigma | Normal |
| −1 | δMTF <− 1 sigma | Worse than normal |

TABLE 3

Clinical 7-MTF-score system

| MTF score | δMTF = MTF − mean (MTF) | Categories |
|---|---|---|
| +3 | δMTF > 3 sigma | superior 3 |
| +2 | 2 sigma < δMTF <= 3 sigma | superior 2 |
| +1 | 2 sigma < δMTF <= 2 sigma | superior 1 |
| 0 | −1 sigma <= δMTF <= 1 sigma | Normal |
| −1 | −2 sigma =< δMTF <− 1 sigma | Inferior 1 |
| −2 | −3 sigma =< δMTF <− 2 sigma | Inferior 2 |
| −3 | δMTF <− 3 sigma | Inferior 3 |

Embodiments may include one or more of the following advantages. The invention methods provide an objective and clinical qualification of an eye's optical quality beyond the conventional visual acuity. Visual acuity in combination with the clinical MTF score will give a compressive representation of vision performance. For example, vision performance of a normal eye is considered superior if its acuity is 20/20 or better and its clinical MTF score is "better than normal." Vision performance of a normal eye is considered normal if its acuity is 20/20 or better and its clinical MTF score is "normal." Vision performance of a normal eye is considered inferior if its acuity is 20/20 or better and its clinical MTF score is "worse than normal." The invention methods can be used for the selection of eyes with exceptional optical quality in the normal population, e.g., for the selection of pilots whose optical quality is critical, for the selection of eyes in the normal population with low optical quality for customized refractive corrections with spectacles, contact lenses, and refractive surgeries, for measuring the benefits of customized refractive corrections with spectacles, contact lenses, refractive surgeries, cataract surgeries beyond acuity, and for a more comprehensive assessment of conventional refractive correction with contact lenses, refractive surgeries, cataract surgeries, corneal transplants.

Methods for Evaluating an Eye's Optical Quality with Variable Pupil Size

Figure 2:
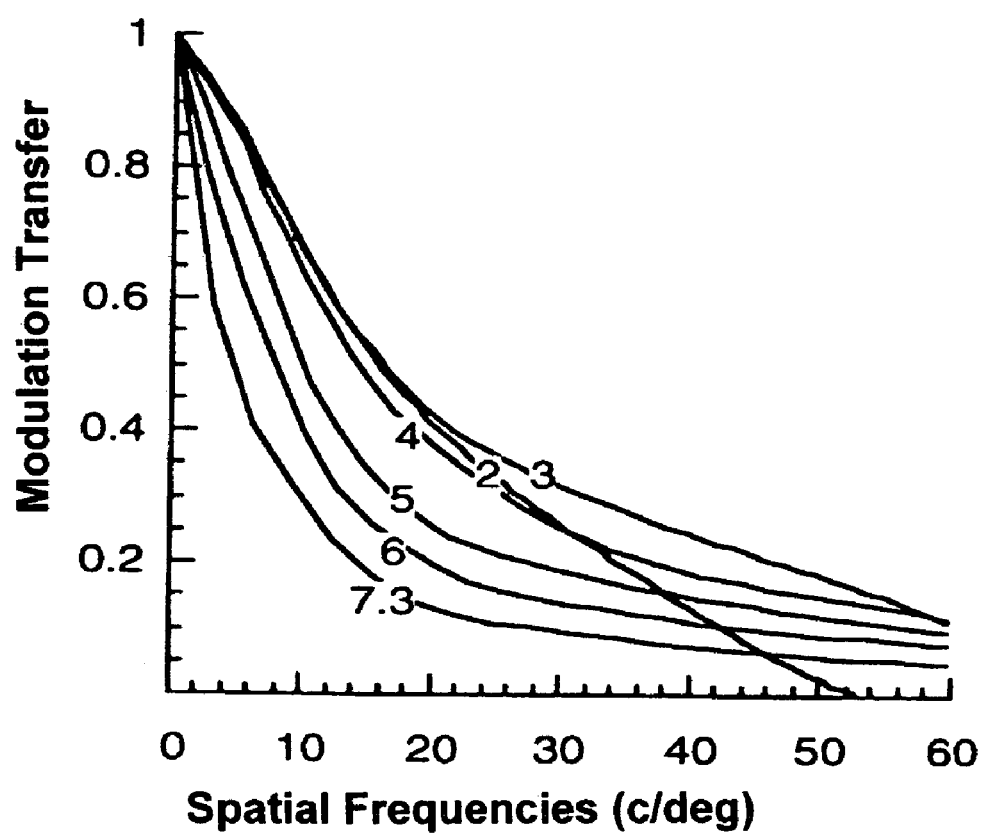
FIG. 2 shows radially averaged MTF of 14 eyes for different pupil sizes that are derived from wavefront measurements from a large dilated pupil (7.3 mm in diameter).

Even with the clinical MTF systems, it is still difficult to compare quality of vision because MTF of different eyes, as shown in FIG. 2, are usually compared at the same pupil size for fairness, even thought such a fair comparison is often meaningless. We propose to evaluate and compare vision and optical quality not at same pupil sizes rather under the same conditions at different pupil sizes.

Three key vision conditions are identified as shown in FIG. 4. They include optics for the diffraction-limited pupil, for the best vision, and for night vision.

First, the Diffraction-Limited Pupil (DLP) is defined as the largest pupil at which the eye's optical quality is still diffraction-limited. An optics system is defined as diffraction-limited if the Strehl Ratio of the point-spread function is 0.8. It is well-known that optics of normal human eyes is diffraction-limited for a small pupil around 2 mm. If an eye's optical quality is far below diffraction limited in the central 2 mm, it is likely that the eye's day vision is problematic. The larger the DLP is, the better the optical quality for day vision.

Second, Best Vision (BV) is defined as the vision of an eye with the best optical quality in all pupil sizes. Best optical quality can be defined as the eye's MTF with the largest frequency bandwidth, although other definitions are also possible. It is well-known that an eye's optical quality is at its best for a pupil size around 3 mm for normal eyes with a conventional sphero-cylindrical correction. When BV is compared, we deal with the ultimate best vision at all pupil size, which may range from 2.5 mm to 4 mm for normal eyes and could be larger with customized corrections of high order aberrations.

Third, night vision should be compared for optical quality in a large natural pupil that can be different from eye to eye. Aberrations of the eye have to be measured with the largest natural pupil instead of a fixed 6 mm pupil or a dilated pupil.

Figure 5:
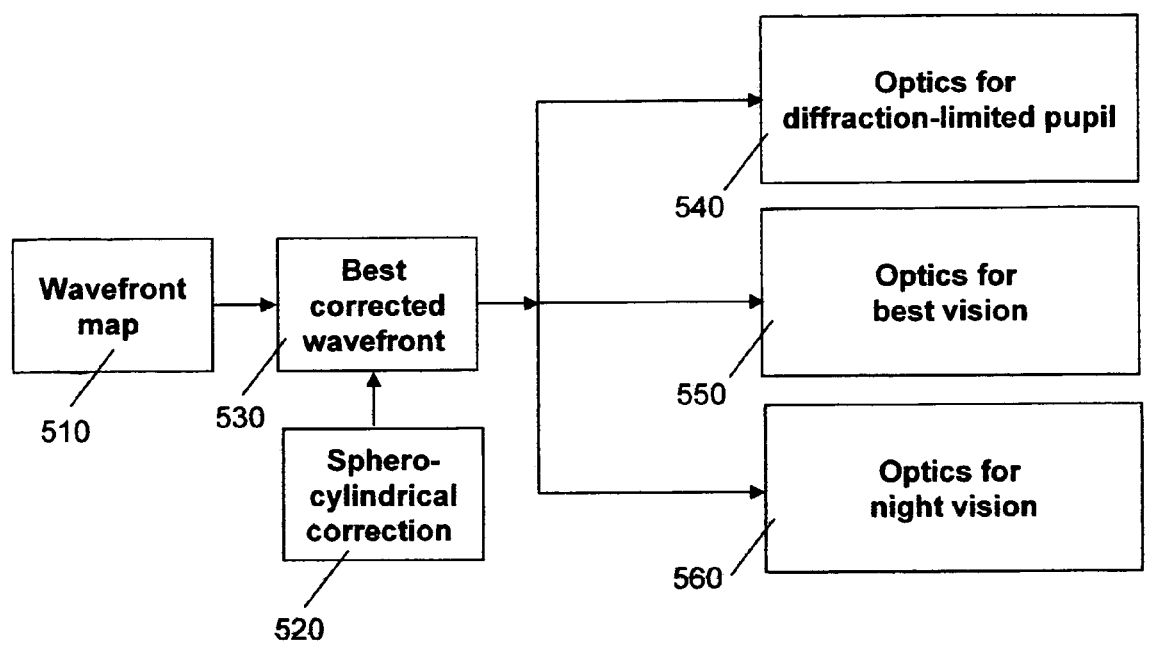
FIG. 5 shows the identified equal conditions for comparing of vision quality at different pupil sizes in accordance with the present invention.

FIG. 5 shows the invention methods for comparing vision performance under equal conditions. Wave aberration of an eye for a large natural pupil is obtained from a wavefront measurement (510). The best corrected wavefront (530) is obtained from the measured wave aberration (510) with a sphero-cylindrical correction (520). Optics of human eyes in a large pupil is divided into three pupil conditions: optics for diffraction-limited pupil (540), optics for best vision (550), and optics for night vision (560). A host of parameters of human eyes including wave aberration, modulation-transfer function as well as point-spread function can be compared under the these equal conditions at different pupil sizes.

A number of embodiments have been described. Nevertheless, it will be understood that various modifications may be made without departing from the spirit and scope of the invention. For example, advantageous results still could be achieved if steps of the disclosed techniques were performed in a different order and/or if components in the disclosed systems were combined in a different manner and/or replaced or supplemented by other components. Accordingly, other embodiments are within the scope of the following claims.

What is claimed is:

1. A method for specifying image quality of an optical object having at least one optical surface, comprising:
   obtaining at least one wave aberration of a tested optical object;
   calculating at least one modulation transfer function from the obtained wave aberration of the tested object;
   obtaining modulation transfer functions from a plurality of other optical objects that are similar to the tested optical object;
   determining image quality of the tested object using a relative score system derived from the calculated modulation transfer function of the optical object and the obtained modulation transfer function from a plurality of optical objects that are similar to the tested optical object.

2. The method of claim 1, wherein the optical object is an eye; and said step of obtaining at least one wave aberration of a tested optical object comprises measuring wave aberration of an eye with an aberrometer including but not limited to a Hartmann-Shack sensor aberrometer.

3. The method of claim 2, wherein a plurality of optical objects comprises a large number of eyes.

4. The method of claim 3, wherein a large number of eyes are under one kind of refractive correction.

5. The method of claim 2, wherein determining image quality of the tested object using a relative score system comprises calculating a ratio of the modulation transfer function of the tested eye to the mean modulation transfer function from a plurality of eyes, and setting a relative score based on the calculated ratio of modulation transfer and the standard deviation of modulation transfer function from a plurality of eyes.

6. The method of claim 2, wherein determining image quality of the tested object using a relative score system comprises displaying and specifying MTF of the eye in a plurality of categories, wherein a plurality of cateaories in one example include "better than normal" if the MTF of the tested eye is more than "the mean MTF plus one standard deviation" of the modulation transfer function for a plurality of eyes, "normal" if the MTF of the tested eye is within "the mean MTF plus and minus one standard deviation" of the modulation transfer function for a plurality of eyes, and "abnormal" if the MTF of the tested eye is less than "the mean MTF minus one standard deviation" of the modulation transfer function for a plurality of eyes.

7. The method of claim 2, wherein a relative score system is represented in percentile by ranking the calculated modulation transfer function of the tested eye against a set of modulation transfer functions from a plurality of eyes.

8. The method of claim 2, further comprises removing a refractive correction including focus error and astigmatism for the determination of the best corrected image quality.

9. The method of claim 2, further comprises specifying image quality for at least one spatial frequencies.

10. The method of claim 2, further comprises specifying total image quality of the tested eye derived from the total volume under a 2D modulation transfer function within a frequency band.

11. The method of claim 10, wherein the frequency band is between 0 cycles/degree and 60 cycles/degree.

12. A method for specifying vision clarity of an eye, the eye having a pupil, comprising:
   obtaining a wave aberration of an eye;

calculating modulation transfer function from the obtained wave aberration of an eye;

obtaining modulation transfer functions from a plurality of other eyes;

specifying vision clarity of the tested eye for a special vision condition using a relative score system derived from the calculated modulation transfer functions of the eye and the obtained modulation transfer functions from plurality of eyes, wherein a special vision condition involves in eyes of different pupil sizes.

13. The method of claim 12, wherein obtaining a wave aberration of an eye comprises measuring at least one wave aberration with an aberrometer including but not limited to a Hartmann- Shack sensor aberrometer.

14. The method in claim 12, wherein a special vision condition is defined by the best optical quality for an eye in all possible pupil sizes.

15. The method in claim 14, wherein the best optical quality for an eye in all possible pupil sizes is determined by calculating modulation transfer functions for a plurality of pupil sizes and finding the largest total volume or area under the calculated modulation transfer functions.

16. The method in claim 14, wherein the best optical quality for an eye in all possible pupil sizes is determined by calculating modulation transfer functions for a plurality of pupil sizes and finding the largest half-height bandwidth of modulation transfer function.

17. The method in claim 12, wherein a special vision condition is the largest pupil diameter measured by an aberrometer for natural eyes without dilation.

18. The method of claim 12, wherein a relative score system is obtained by calculating a ratio of the modulation transfer function of the tested eye to the mean value of obtained modulation transfer function from a plurality of other eyes.

19. The method of claim 12, wherein a relative score system is ranked in percentiles.

20. The method of claim 12, wherein specifying vision clarity of the tested eye is for at least one spatial frequencies such as 30 cycles/degree.

* * * * *